US00RE44595E

(19) United States
(12) Reissued Patent
Cadio et al.

(10) Patent Number: US RE44,595 E
(45) Date of Reissued Patent: Nov. 12, 2013

(54) DIAGNOSTIC DEVICE WITH DISPLAY MODULE AND LEVERAGED COMPONENT CONNECTIONS

(71) Applicant: Roche Diagnostics Operations, Inc., Indianapolis, IN (US)

(72) Inventors: Michel Cadio, Carmel, IN (US); Bryan Rolfs, Chicago, IL (US); Aleksey Pirkhalo, Chicago, IL (US); James Wolford, Chicago, IL (US)

(73) Assignee: Roche Diagnostics Operations, Inc., Indianapolis, IN (US)

(21) Appl. No.: 13/749,331

(22) Filed: Jan. 24, 2013

Related U.S. Patent Documents

Reissue of:
(64) Patent No.: 8,226,890
Issued: Jul. 24, 2012
Appl. No.: 12/266,216
Filed: Nov. 6, 2008

(51) Int. Cl.
*G01N 33/00* (2006.01)

(52) U.S. Cl.
USPC ..... 422/82.01; 422/565; 422/566

(58) Field of Classification Search
USPC ..... 422/82.01, 565, 566
See application file for complete search history.

(56) References Cited

U.S. PATENT DOCUMENTS

| | | | | |
|---|---|---|---|---|
| 4,113,342 | A * | 9/1978 | Andreaggi | 439/630 |
| 6,356,321 | B1 * | 3/2002 | Ogawa | 349/58 |
| 6,635,167 | B1 * | 10/2003 | Batman et al. | 205/775 |
| 2008/0277280 | A1 * | 11/2008 | Riebel et al. | 204/406 |

FOREIGN PATENT DOCUMENTS

JP 59018927 A2 1/1984

OTHER PUBLICATIONS

International Preliminary Report on Patentability, PCT/EP2009/007883; Jun. 10, 2010.
International Search Report and Written Opinion, PCT/EP2009/007883; Jun. 10, 2010.

* cited by examiner

*Primary Examiner* — Sam P Siefke
(74) *Attorney, Agent, or Firm* — Harness, Dickey

(57) ABSTRACT

The present invention provides an innovative means for efficient and secure component assembly and for ensuring secure electrical connections in a small diagnostics device where available space for fasteners is limited. In one embodiment, principles of leverage are employed to produce a force at a location where space is available. The force is transferred to a different location of the assembly where it is used to maintain secure connections between components.

26 Claims, 9 Drawing Sheets

DIAGNOSTIC DEVICE WITH DISPLAY MODULE AND LEVERAGED COMPONENT CONNECTIONS

Matter enclosed in heavy brackets [ ] appears in the original patent but forms no part of this reissue specification; matter printed in italics indicates the additions made by reissue.

BACKGROUND

The present invention relates to a diagnostic device, such as a blood analyte meter, and a method of assembly of the same.

Hand held diagnostic devices are often used by patients for "self-testing" for the presence and/or concentrations of selected analytes in test samples. For example, a wide variety of hand held devices or "meters" are available to measure glucose concentrations in whole blood, thus enabling a diabetic to monitor his or her blood sugar level. These meters typically work in conjunction with test strips, the latter of which normally include a reaction chamber into which a reagent composition has been deposited and into which a sample of the patient's blood is drawn by capillary action.

Generally, these test strips and meters operate by optical methods or electrochemical methods. Optical methods generally involve spectroscopy to observe the spectrum shift in the fluid caused by concentration of the analyte, typically in conjunction with a reagent that produces a color change in the strip when combined with the analyte. Electrochemical methods generally rely upon the correlation between a current (amperometry), a potential (potentiometry) or accumulated charge (coulometry) and the concentration of the analyte, typically in conjunction with a reagent that produces charge-carriers when combined with the analyte. The diagnostic device makes the appropriate correlation and displays the result of the test, e.g., blood glucose concentration.

Current trends in such meters and test strips involve smaller test samples and faster analysis times. Accordingly, the size of test strips and the meters or devices which read them is also trending smaller. This provides a significant benefit to the patient, allowing the use of smaller blood samples that can be obtained from less sensitive areas of the body. Additionally, faster test times and more accurate results enable patients to better control their blood sugar level. Of course, smaller meters are less cumbersome and are able to be stored in small spaces, such as pockets in shirts or trousers, while allowing room for other traditional items such as car keys, coins and the like.

The trend toward smaller meters has introduced challenges in manufacturing. As the overall size of the meter decreases, the components within the meters also become smaller. The challenges arise in large scale assembly and in maintaining the ultimate structural integrity of the meter, e.g., its ability to withstand a drop test. These challenges are caused in part by the fact that as sizes become smaller, the number of fasteners such as screws and clips that can be used decreases as does the ability to efficiently install them during full scale manufacturing.

Similarly, the assembly of a meter is generally affected by the interconnection of the electrical circuitry, which is generally mounted onto flat, substantially two-dimensional circuit boards with attached components to carry, control, select, store and manipulate electronics signals. The greatest potential for system failure typically occurs at the location of the interconnections of the components, circuit boards and wiring assemblies. As meter size becomes smaller it becomes increasingly difficult to accurately align the components and maintain the connections secure, which in turn produces increased risk of failed connections.

SUMMARY OF THE INVENTION

The present invention provides innovative solutions for efficient and secure component assembly and for ensuring secure electrical connections in a small diagnostics device where available space for fasteners is limited. In one embodiment, principles of leverage are employed to produce a force at a location where space is available. The force is transferred to a location of the assembly remote from where it is created and is used to maintain secure connections between components.

In one embodiment, a diagnostic device, e.g., a blood glucose meter, is provided. The diagnostic device includes a housing having an upper housing part and a lower housing part. A display module is mounted in the housing, and a circuit board is positioned between the display module and the lower housing part. A lever arm extends from a first section of the display module in a direction away from the display module. A contact portion of the lever arm is biased against the circuit board or the lower housing part and produces a force that is transferred to a second section of the display module that is remote from the first section.

The diagnostic device typically includes one or more fasteners that secure the display module to the housing. The fasteners are positioned remote from the second section of the display module, and in certain embodiments are located near the first section or end of the display module. Similarly, the lever arm may comprise two or more lever arms.

In certain embodiments, the force produced by the lever arm is used to bias an electrical connector of the display module to an electrical connector of the circuit board, thereby decreasing the risk of failure of this electrical connection.

In another embodiment, a method is provided for assembling a small diagnostic device having upper and lower housing parts, a display module, and a circuit board. In this method, the circuit board is inserted into the lower housing part, and the display module is placed over the circuit board such that a lever arm extending from a first section of the display module is biased against the circuit board. The display module is fastened to the lower part of the housing, wherein a force is transferred from the lever arm to a second section of the display module that is remote from the first section. The force biases the second section of the display module against the circuit board. The upper housing part is then secured to the lower housing part.

The force that is transferred to the remote part of the display module obviates the need for fasteners there. This is advantageous when space for fasteners in this remote location is limited or when installing the fasteners would be inefficient during manufacture. This method also enables substantially all movement of the circuit board and display module relative to the lower housing part during manufacture to be substantially in a single direction, namely, downward, which in turn improves manufacturing efficiencies.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

Figure 1A:
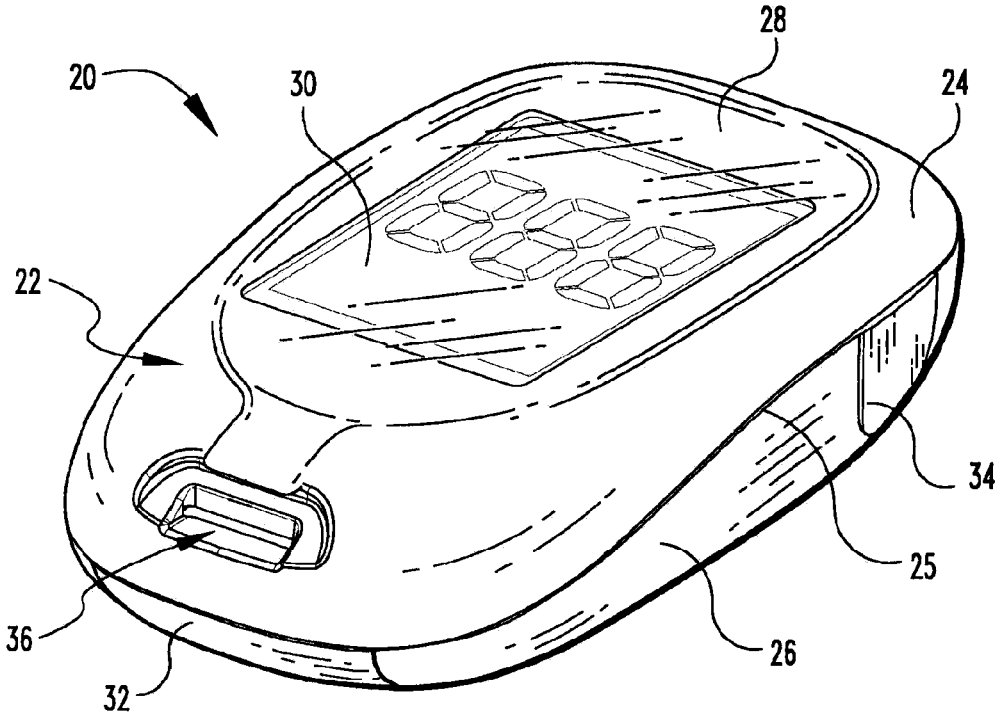
FIG. 1A is a perspective view of a diagnostic device in accordance with one embodiment of the present invention.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Turning now to FIG. 1, a diagnostic device or meter 20 is shown. Device 20 may be used, e.g., to determine and display a blood analyte concentration, such as glucose concentration. The meter 20 has a housing 22, which is formed of an upper housing part 24 joined at seam 25 to lower housing part 26. While devices 20 may vary significantly in size, typical dimensions of a meter 20 like the one illustrated can be about 70 mm length, about 43 mm width and about 20 mm depth. Although hooks and clips are employed in the illustrated embodiment to secure parts 24 and 26 (as described below), the upper and lower housing parts 24 and 26 can be secured together by any number of methods known to one of skill in the art, e.g., heat or sonic welding, adhesives, or various "snap fit" configurations. Device 20 includes a window 28 that is aligned with a substantially planar display 30. Window 28 may be formed of a clear plastic material and integrated into upper housing part 24, as is known in the art. A slidable drawer 32 is provided as a battery compartment, flexible buttons 34 (also see FIGS. 1B-1D) are provided to control the device, and a test port 36 is provided that receives a biosensor or test strip (not shown). The device 20 pictured in FIG. 1A uses an amperometric test strip such as that sold under the Accu-Chek® Aviva brand name, available from Roche Diagnostics, Inc. However, device 20 could be configured for other types of test strips, e.g., photometric.

Figure 1B:
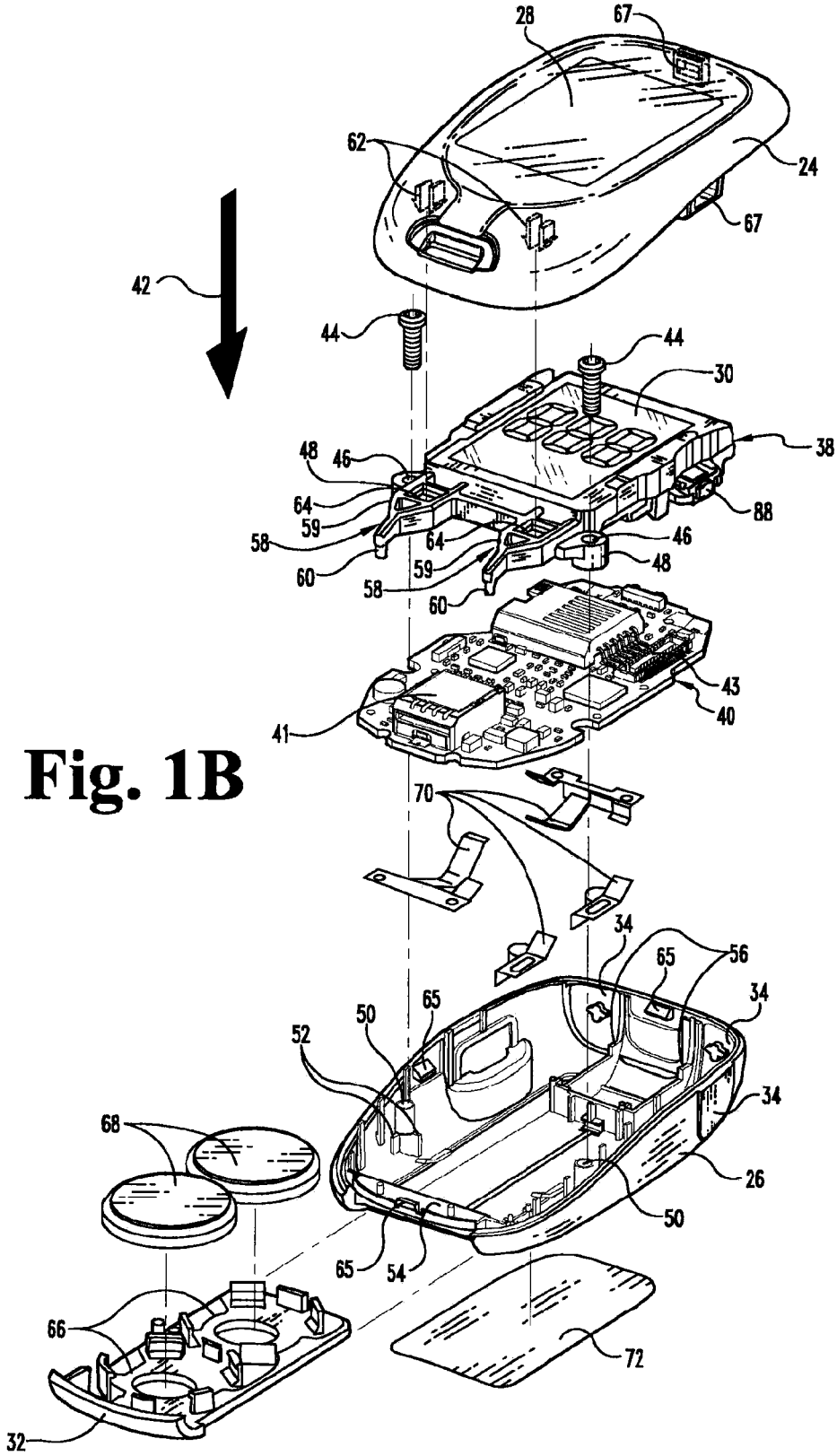
FIG. 1B is an exploded perspective view of the diagnostic device of FIG. 1A.

The general arrangement of the interior components of device 20 can be understood with reference to FIG. 1B. An LCD display module 38 and printed wiring board (PWB) 40 are positioned between the upper housing part 24 and lower housing part 26. While an LCD display module is illustrated in the exemplary embodiment, it is to be understood that these teachings can be utilized with other display modules, e.g., light emitting diode (LED), organic light emitting diode (OLED), plasma, and the like. In the same vein, while board 40 is illustrated in the exemplary embodiment as a printed wiring board, these teachings could be employed for a wide variety of circuit boards whose physical placement and assembly raises design challenges due to limited space.

Figure 1C:
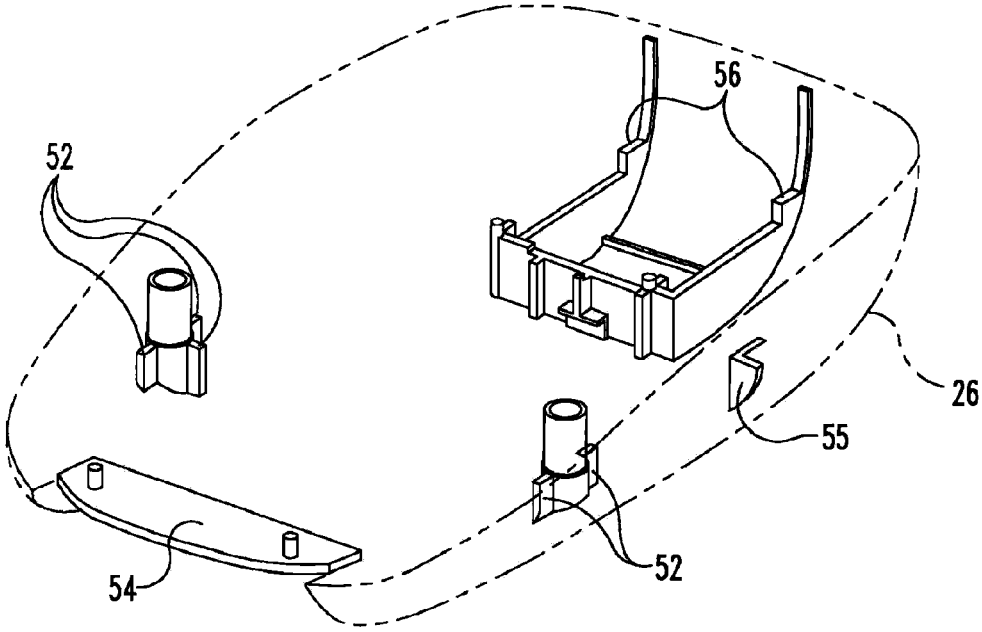
FIG. 1C is a perspective view of the lower part of a housing of the device depicted in FIG. 1A showing components that support the bottom surface of a printed wiring board, the lower housing part being shown in phantom.
Figure 1D:
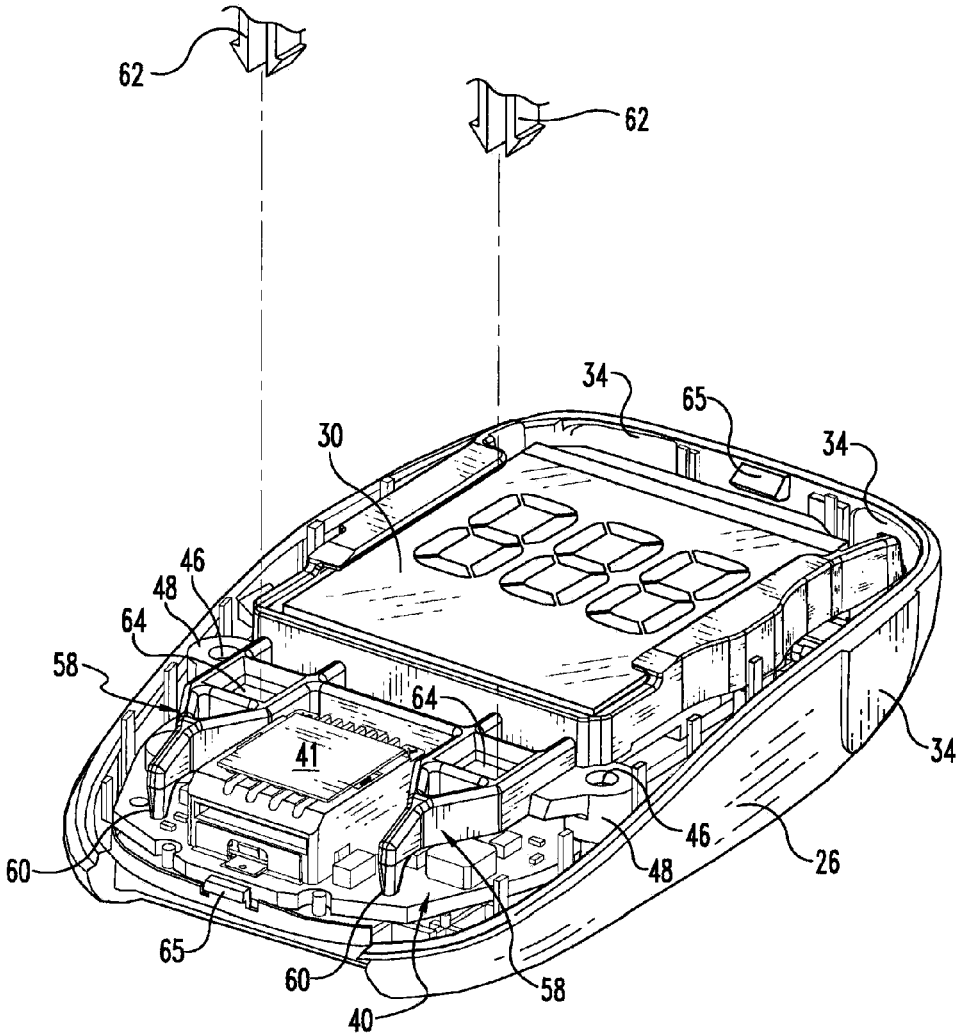
FIG. 1D is a perspective view of the device depicted in FIG. 1A, essentially assembled, but with the top housing part not shown and with clips from the top housing shown exploded away.

As shown in FIGS. 1B and 1D, a module 41 for receiving and analyzing a test strip is mounted on PWB 40. PWB also includes an electrical connector 43 whose connection to the LCD display module 38 is secured by a creative application of leverage, as described in detail below. As also explained in further detail below, PWB 40, LCD display module 38 and upper housing part 24 are brought together substantially in a single vertical direction, as indicated by arrow 42 in FIG. 1B. Screws 44 are received through cylindrical bores 46 defined through bosses 48 and are threadingly received in threaded bores 50 formed in lower housing part 26. When screws 44 are tightened, the bottom of PWB 40 is pressed by LCD display module 38 against various support structure in lower housing part 26, such as fins 52, shelf 54 and fins 56 shown in FIG. 1D. While the fasteners 44 in the exemplary embodiment are shown as machine screws, one of skill in the art would readily recognize that other fasteners can be employed.

LCD display module 38 has a pair of innovative lever arms 58 extending from it. The lever arms have a portion 59 that extend away from the periphery of display module 38 and in the illustrated embodiment are substantially parallel to the plane of the display 30. Lever arms 58 also have nubs or contact portions 60 which are substantially orthogonal to portions 59. The contact portions 60 press against PWB 40 when the device is assembled, producing a force that can be transferred to a section of the display module 38 remote from lever arms 58, as explained in more detail below.

As alluded above, the housing parts 24 and 26 are secured together by four hooks 65 (three shown in FIG. 1B) arranged on bottom housing part 26 which engage receptacles 67 (two shown in FIG. 1B) extending from upper housing part 24. Additionally, a pair of clips 62 (shown in phantom in FIG. 1B) project downwardly from the upper housing part 24 and lock into square receptacles 64 formed in lever arms 58. Clips 62 advantageously tie together the components of device 20 and provide a more secure overall assembly than if only hooks 65 and clips 67 were employed.

With further reference to FIG. 1B, slidable drawer 32 defines spaces 66 for batteries 68. When drawer 32 with batteries 68 is slid into the housing part 26, battery contacts 70 provide an electrical connection to the corresponding connectors (not shown) on the bottom of PWB 40. Batteries 68 can be a lithium ion type battery and connectors 70 can be formed from copper or another suitable conductor, as is known in the art. A label 72 is provided to be adhered to the underside of the bottom housing part 26 and can be used for various identifying markings, instructions, warnings, company logos or other information.

Turning now to FIGS. 2A-2D, the inventive LCD display module 38 and its method of assembly can be understood. Display module 38 includes a frame 80 and a display assembly 82. Frame 80 has a first end or section 84 from which lever arms 58 extend, and a second end 86, that is positioned substantially opposite first end 84. In the illustrated embodiments, lever arms 58 are integrally formed with frame 80. Bosses 48 are positioned close to end 84 and remote from end 86. Frame 80 can be formed from any of a wide variety of materials, particularly, polycarbonate, polystyrene, ABS or other materials.

Display assembly 82 includes an LCD display screen 30 adhered to a backlight 90 by, e.g., a doubled sided tape. Any of a wide variety of LCD displays and backlights can be used for device 20. A printed circuit board ("PCB") 92 connects to PWB 40 through connector 94 and allows device 20 to be controlled through switches 88, which are accessed through flexible buttons 34 (FIGS. 1B and 1D) in the assembled device. A flexible cable 96 is connected by conventional "hot bar" soldering to PCB 92 and screen 30.

The sides of frame 80 define grooves or channels 98 in which display assembly 82 is slidably received and mounted. Assembly 82 is pressed against shelf 100 on its bottom edge and on its top edge is secured by clip 102. Protrusion 104 is biased forwardly (out of the page in FIG. 2A) and presses against the back of backlight 90 to bias assembly 82 within frame 80 and prevent rattle.

Figure 2A:
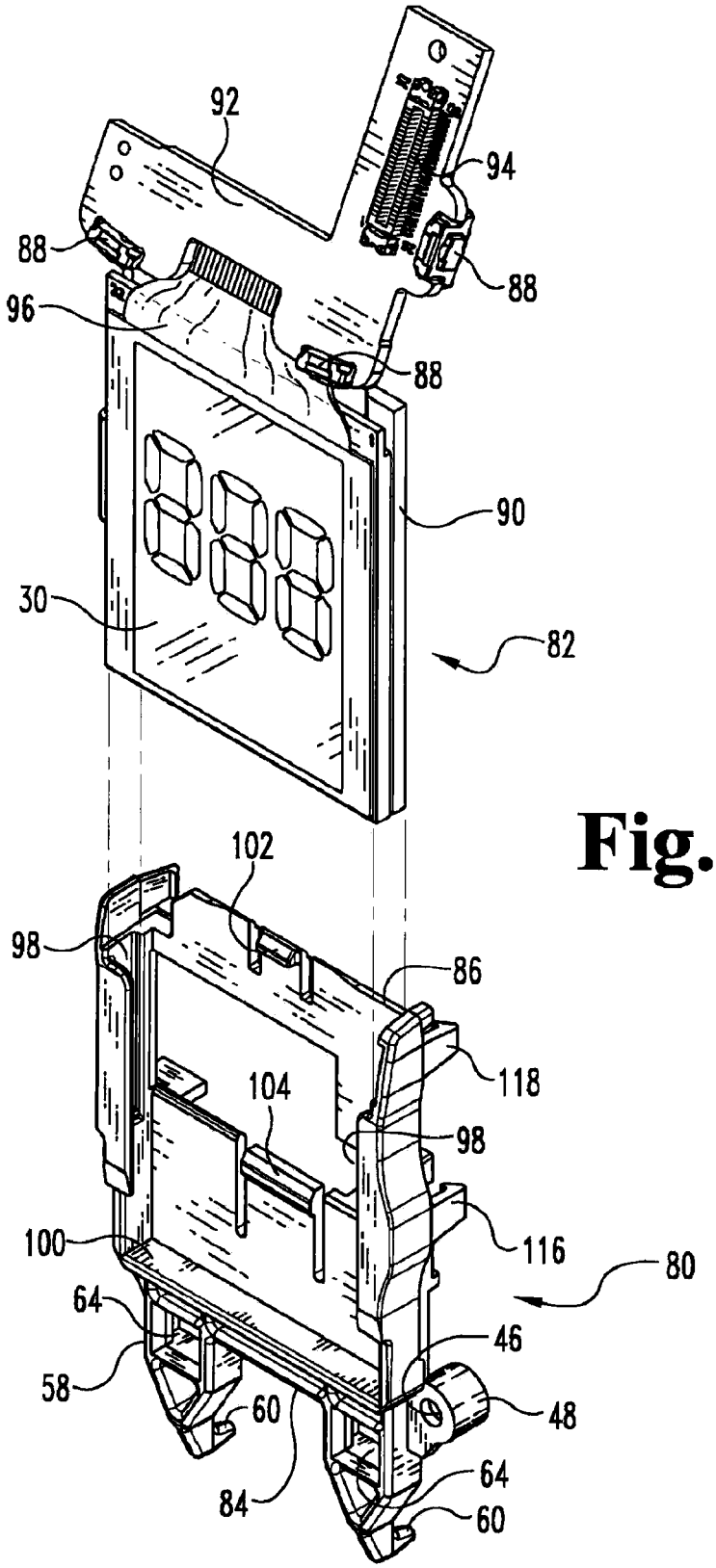
FIGS. 2A-2D are various perspective views of a liquid crystal display ("LCD") display module suitable for use with the diagnostic device illustrated in FIG. 1A and the assembly of such LCD display module.
Figure 2B:
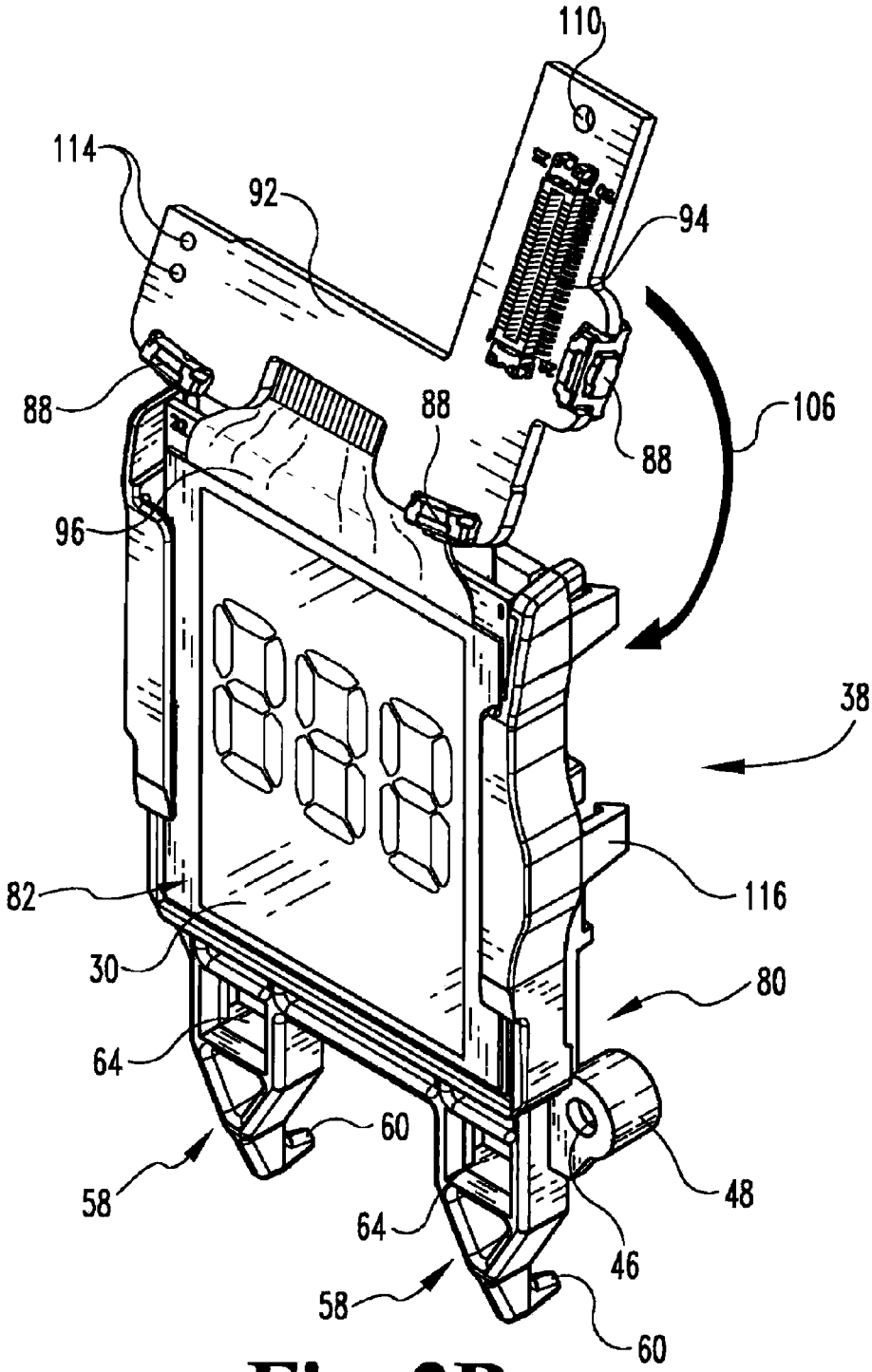
Figure 2D:
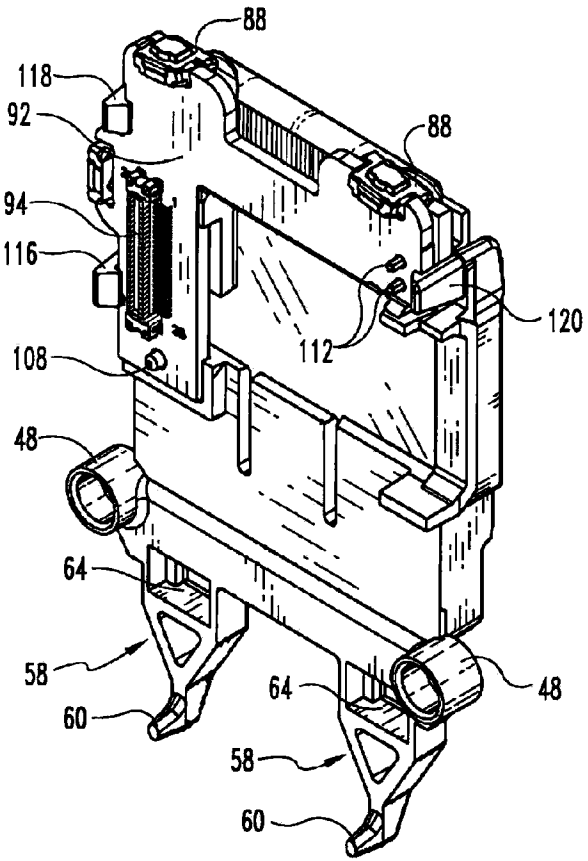
Figure 2C:
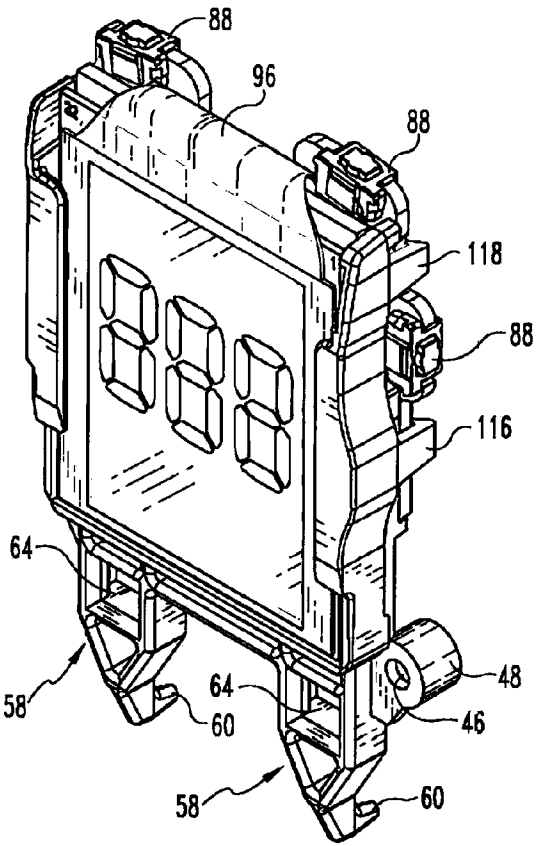

FIG. 2B illustrates the LCD display module 38 after assembly 82 has been slidably mounted within frame 80, but before PCB 92 has been secured in place. PCB 92 is movable or pivotable in the direction of arrow 106 by virtue of flexible cable 96. PCB 92 is pivoted during assembly from the position shown in FIG. 2B to that shown in FIGS. 2B and 2C. A centering pin 108 (FIG. 2D) aligns with and is inserted through alignment hole 110. Optionally, as shown in FIG. 2D, connection pins 112 may be provided that extend from the backlight 90 and extend through holes 114. Pins 112 perform the dual functions of electrically connecting the backlight to the PCB 92 and properly aligning the PCB with respect to the display module. If provided, pins 112 would be soldered during assembly of device 20. One of skill in the art should understand that the connection to the backlight 90 could also be provided through another flex cable (not shown) originating from the backlight and soldered or hot barred to PCB 92, thereby obviating the need for pins 112.

Figure 3:
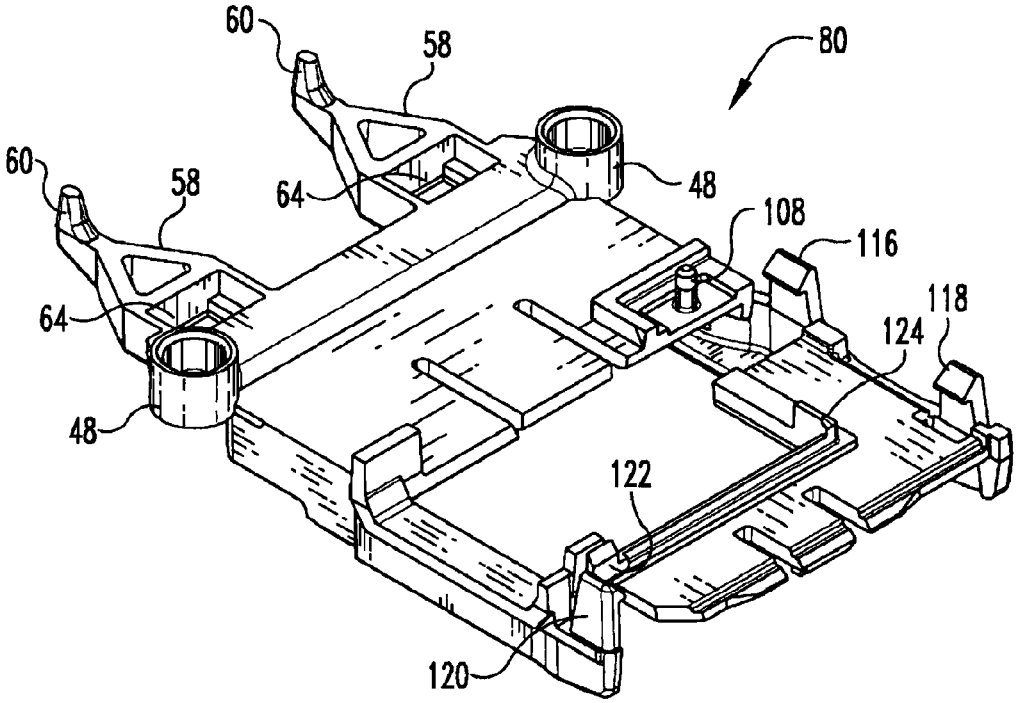
FIG. 3 is a rear perspective view of the frame of the LCD display module illustrated in FIG. 2A-2D.

As noted above, accurate placement of components is important to ensure the integrity of the electrical connections, in this case, the connection of connector 94 to connector 43 of PWB 40. To facilitate this connection, PCB 92 must be accurately placed relative to frame 80 and LCD display module 38. Thus, in addition to pin 108, there are provided three clips 116, 118 and 120 shown in FIGS. 2D and 3 which position the PCB 92. Clips 116, 118 and 120 also secure PCB 92 to frame 80. Additionally, the position of stop 122 can be controlled within a tight tolerance during manufacture of frame 80. When PCB 92 is snapped into frame 80, it abuts against stop 122, which accurately positions it with respect to frame 80.

As noted above, the small size of device 20 poses challenges in design and assembly. That is, there is little room available for fasteners and limited room in the housing 22 to form receptacles into which such fasteners could be secured. Furthermore, the placement of fasteners must be carefully considered to ensure that the assembly of the major components of device 20, namely, PWB 40, display module 38 and upper housing part 24 can be substantially straight down. Having to move one or more of these parts laterally during assembly, e.g., to secure a fastener, could significantly decrease manufacturing efficiency. On the other hand, and as also noted above, accurate placement of the components is important to avoid failure of electrical connections.

To address these issues, LCD display module 38 is provided with two lever arms 58, as described above, which project or extend away from the bottom side or section 84 of frame 80. By an innovative use of leverage, these lever arms obviate the need for fasteners at the top end 86 of the frame where space is unavailable. This can perhaps be best appreciated with reference to FIG. 4, which is a side elevational view of PWB 40 and display module 38, with certain parts not shown for purposes of clarity. As discussed above and illustrated in FIG. 4, PWB 40 is supported on its bottom side by a series of fins (52, 55 and 56) and a shelf 54 formed in bottom housing part 26. Screw 44, when tight, firmly sandwiches the PWB 40 between boss 48 and fins 52. In this arrangement, the substantially planar display 30 that is held by frame 80 is substantially parallel with PWB 40. The portion 59 of lever arm 58 is thus substantially parallel to PWB 40 and display 30, and portion 59 extends away from frame 80 of display module 38. That is, frame 80 defines a periphery of the display 30, and lever arms 58 extend away from this periphery.

In the exemplary embodiment, the lever arm is "preloaded," meaning that it is biased downwardly in the direction of arrow 133. Such a "pre-load" can be created, e.g., by flexing arm member slightly upward during installation as is indicated by its unflexed or rest position 131 shown in phantom in FIG. 4, which position 131 may be shown exaggerated for purposes of illustration. Thus, when screw 44 is tightened during manufacture, contact portion 60 is pushed upwardly with a force that is equal and opposite to the downward biasing force created by the preload. This upward force is indicated by arrow 128. For purposes of explanation, it is helpful to think in terms of a "pseudo moment" 130 about boss 48, whereby some of the force pushing lever arm 58 upward is transferred to a section 135 of the display module 38 that is remote from the end 84 of the frame and remote from the location where lever arm 58 contacts PWB 40.

The downward force produced on remote section 135 of display module 38 is represented as arrow 136, and this force is advantageously focused where it is needed, namely, the connection between electrical connector 43 of PWB 40 and connector 94 of display module 38. That is, the lever arm 58 utilizes leverage principles to produce equal and opposite forces represented by arrows 136 and 138, which in turn creates a stable and secure connection between electrical connectors 94 and 43—without requiring any fasteners located close to the electrical connectors. (While the forces are shown as discrete arrows 136 and 138 in FIG. 4, a skilled artisan will appreciate that the forces securing the electrical connectors create a pressure that is applied over the entire portions of the connectors that contact one another.) As shown, spaces 134 are provided between clips 116 and 118 and PWB 40 (as well as other structure from display module 38 and PWB 40) so that the forces securing connectors 43 and 94 are maximized. In this manner, one of skill in the art can appreciate that available space outside the periphery of the display is utilized for lever arms 58. This in turn produces a force that is creatively transferred to a remote location of display module 38 where it is needed because room for fasteners in this remote location is unavailable.

In addition to maintaining the electrical connection secure, the force provided by lever arms 58 also prevents damage to the device 20 when it is dropped. In particular, if the lever arms 58 were not provided, during a drop test the acceleration forces encountered by the LCD module 38 would tend to push it forward and, after it is rotated or pivoted about screws 44, the module 38 may collide with the front of the housing 22 and break. The forces induced by lever arms 58 counteract these acceleration forces during a drop test and thereby prevent the LCD module from hitting the housing.

Figure 4:
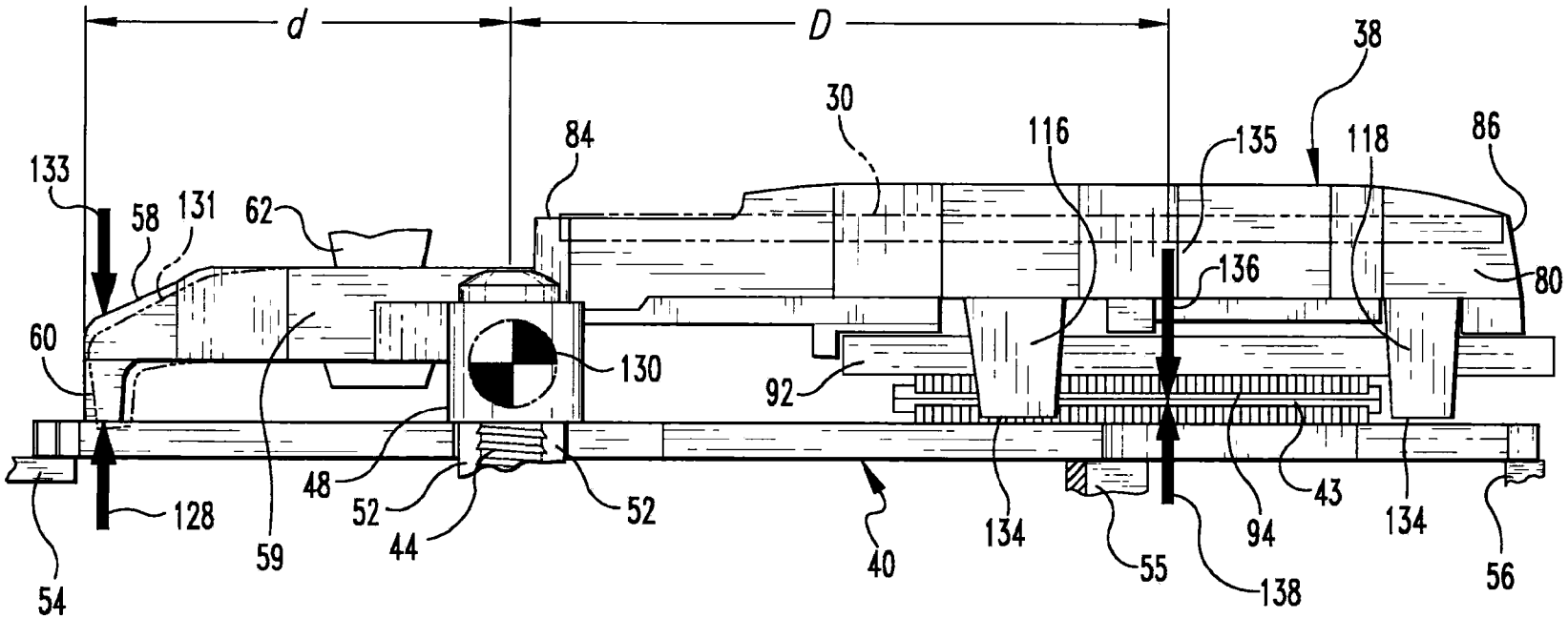
FIG. 4 is a side elevational view illustrating the LCD display module installed over the PWB.

The preload force on lever arms 58 is relatively strong, thereby creating a quite stable lever arm 58 having a portion 59 that provides significant resistance to movement. Exemplary embodiments utilize the stability of lever arms 58 by connecting them to top housing part 24 through clips 62. A portion of a clip 62 is shown in FIG. 4. Of course, the clips may be formed on arm 58 and the receptacles in the upper housing 24, the point being that this connection is especially stable and also structurally ties together the interior components with the housing in which the reside, thereby creating an overall more stable device 20.

One of skill in the art would recognize many possible variants of the embodiment just discussed to utilize these teachings. For example, while the contact portion 60 abuts against board 40, this need not necessarily be the case. In certain designs, it may instead be desirable to have the contact portion extend through the board 40 and abut the lower housing.

Furthermore, the lever arms 58 are illustrated in the exemplary embodiment as having a specific shape, but one of skill in the art would readily recognize many variations and modifications that could be made to arms 58. Generally, arms 58 extend away from the fulcrum or moment 130 and also extend away from the periphery of frame 80. Arms 58 also must have a portion 60 that contacts board 40 or bottom housing part 26 to create a force that can be transferred. Lever arms 58 will thus typically have a shape resembling a cantilever arm, although one of skill in the art would recognize many variations of this cantilever shape. Also, while two lever arms are illustrated herein, in other circumstances one or perhaps three or more lever arms could be employed. Furthermore, the location of the lever arms, i.e., where in particular they project from the frame, depends upon the specific configuration of the device in which these teachings are employed.

The length or distance "d" shown in FIG. 4 may of course vary depending upon space available in the specific design. Where "d" may be configured rather large, the amount of preload needed to produce the desired force at the remote section may be reduced, and vice versa. In the same vein, the distance "D" is also a variable that may vary depending upon the specific display modules and circuit boards of the particular design and the space available for these components.

As one of skill in the art will recognize, the magnitude of the forces applied at the remote sections such as section 135 is roughly proportional to the ratio of d/D. In the embodiment shown in FIG. 4, the distance "d" is significantly smaller than distance "D," which is the reverse of a typical lever-fulcrum application. Surprisingly, however, as shown in FIG. 4, even when distance "D" is significantly greater than distance "d," sufficient force is produced by the lever arms to secure the electrical connectors. Generally, these teachings may be used when the ratio of d/D is small, although the smaller the ratio, the less effective is the production and transfer of force. Additionally, small ratios may pose challenges in identifying and selecting a material that would provide sufficient flexibility without exceeding its limit of elasticity.

Eliminating fasteners at the remote section 135 of the display module allows an efficient method of assembling the major components in which substantially all movement of the board 40, display module 38 and upper housing part 24 relative to the lower housing part 26 is substantially in a single direction, namely downward. Thus, during assembly, as a first step the PWB 40 can be inserted into the lower housing part 26. Next, the display module 38 is placed over the circuit board, such that lever arms 58 arm extend from end 84 and are biased against PWB 40. Fasteners 44 are then inserted into bores 46 (FIG. 1B), which secures the PWB 40 and display module 38 in the housing. In this manner, as fasteners 44 are drawn tight, a force is created and is transferred from the lever arms 58 to the section 135 of the display module that is remote from the section 84 and is even further remote from the contact portions 60 of lever arms 58.

Advantageously, the force that is created (see arrows 136 and 138 in FIG. 4) biases the section 135 of the display module against the PWB 40, and more specifically, biases the electrical connectors 94 and 43 together. As noted, upper housing 24 is secured to the lower housing 26 by virtue of the clips 65 and hooks 67, and the major components of the device are further tied together and secured by means of the clips 62 that fit into receptacles 64. As discussed above, the frame 80 and display assembly 82 are separate components, such that the display assembly 82 can be slid into frame 80 before display module 38 is installed into device 20.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A diagnostic device, comprising:

a housing having an upper housing part and a lower housing part;

a display module mounted in the housing and comprising a fulcrum connected to the lower housing part;

a circuit board positioned between the display module and the lower housing part; and a cantilever arm extending from a first section of the display module in a direction away from the fulcrum and away from a periphery of the display module, a contact portion of the cantilever arm being biased against the circuit board or the lower housing part;

wherein the bias of the cantilever arm produces a force that is transferred to a second section of the display module remote from the first section.

2. The diagnostic device of claim 1, further comprising a fastener securing the display module to the housing, the fastener positioned remote from the second section of the display module.

3. The diagnostic device of claim 2, wherein the fastener comprises a pair of fasteners positioned near the first section of the display module.

4. The diagnostic device of claim 1, wherein the lever arm comprises a pair of lever arms.

5. The diagnostic device of claim 1, wherein the display module comprises a first electrical connector and the circuit board comprises a second electrical connector, wherein the force produced by the lever arm biases the first connector and the second connector together.

6. The diagnostic device of claim 1, wherein the display module comprises a substantially planar display screen and the circuit board is positioned substantially parallel to the display screen.

7. The diagnostic device of claim 6, wherein the lever arm has a first portion that extends substantially parallel to the display screen, the contact portion extending toward the circuit board.

8. The diagnostic device of claim 1, wherein the contact portion contacts the circuit board.

9. The diagnostic device of claim 1, wherein one of the upper housing part and the lever arm comprises a clip extending therefrom, the clip connecting the lever arm to the upper housing part and biasing the upper housing part closed.

10. The diagnostic device of claim 1, wherein the display module comprises an LCD display module.

11. The diagnostic device of claim 1, wherein the display module comprises a frame, the lever arm being integrally formed with the frame.

12. The diagnostic device of claim 11, wherein the frame comprises an opening through which a fastener extends.

13. The diagnostic device of claim 11, wherein the display module is slidably mountable in the frame.

14. A diagnostic device, comprising:

a housing having an upper housing part and a lower housing part;

a display module mounted in the housing and having a first end and a first electrical connector remote from the first end;

a lever arm extending from the first end and producing a force remote from the first electrical connector;

a circuit board positioned between the display module and the lower housing part and having a second electrical connector connected to the first electrical connector; and a fulcrum connected to the display module and located remote from the first end, wherein the force is transferred from the lever arm through the fulcrum to the first and second electrical connectors to bias the first and second electrical connectors together.

15. The diagnostic device of claim 14, wherein the lever arm has a contact portion biased against the circuit board.

16. The diagnostic device of claim 15, wherein the lever arm comprises a pair of lever arms.

17. The diagnostic device of claim 14, further comprising a fastener securing the display module to the housing, the fastener positioned near the first end.

18. A method of assembling a diagnostic device having upper and lower housing parts, a display module, and a circuit board, the method comprising:

(a) inserting the circuit board into the lower housing part;

(b) placing the display module over the circuit board, such that a lever arm extending from a first section of the display module is biased against the circuit board or the lower housing part;

(c) fastening the circuit board to the lower housing part and thereby creating a fulcrum, wherein a force is transferred from the lever arm through the fulcrum to a second section of the display module that is remote from the first section, the force biasing the second section of the display module against the circuit board or the lower housing part; and (d) securing the upper housing part to the lower housing part.

19. The method of claim 18, further comprising fastening the upper housing part to the lever arm.

20. The method of claim 18, wherein substantially all movement of the circuit board and display module relative to the lower housing part during steps (a) and (b) is substantially in a single direction.

21. The method of claim 18, wherein step (c) comprises inserting a fastener through a bore in the frame and into the lower housing part, the fastener being located remote from the second section of the display module.

22. The method of claim 18, further comprising sliding a display assembly of the display module into a frame of the display module before step (b).

23. The method of claim 18, further comprising using the force to bias an electrical connector of the display module to an electrical connector of the circuit board.

*24. A diagnostic device, comprising:*

*a housing having an upper housing part and a lower housing part;*

*a module mounted in the housing and connected at a connection point to the lower housing part;*

*a circuit board positioned between the module and the lower housing part; and*

*a lever arm configured to pivot about the connection point and having a first end extending from a first section of the module in a direction away from the connection point and away from a periphery of the module, the first end of the cantilever arm being biased against either the circuit board or the lower housing part such that the bias of the lever arm produces a force that is transferred to a second section of the module remote from the first section.*

*25. The diagnostic device of claim 24 wherein the module includes a first electrical connector and the circuit board includes a second electrical connector, such that the force produced by the biasing of the lever arm biases the first connector and the second connector together.*

*26. The diagnostic device of claim 24 wherein the module is substantially planar and the circuit board is positioned substantially parallel to the module.*

* * * * *

UNITED STATES PATENT AND TRADEMARK OFFICE

CERTIFICATE OF CORRECTION

PATENT NO. : RE44,595 E
APPLICATION NO. : 13/749331
DATED : November 12, 2013
INVENTOR(S) : Cadio et al.

It is certified that error appears in the above-identified patent and that said Letters Patent is hereby corrected as shown below:

In the Specification

Column 3, line 18, delete “FIG.”, insert --FIGS.--.

Column 4, line 14, delete “FIG. 1D,”, insert --FIG. 1C--.

Column 4, line 57, delete “end”, insert --first end--.

Column 4, line 57, delete “end”, insert --second end--.

Column 6, line 19, delete “end”, insert --first end--.

Column 7, line 51, before “extend”, delete “arm”.

Column 7, line 51, delete “end”, insert --first end--.

Signed and Sealed this
Seventeenth Day of June, 2014

Michelle K. Lee

Michelle K. Lee
*Deputy Director of the United States Patent and Trademark Office*